US 6,678,398 B2

(12) United States Patent
Wolters et al.

(10) Patent No.: US 6,678,398 B2
(45) Date of Patent: Jan. 13, 2004

(54) DUAL MODE REAL-TIME SCREENING AND RAPID FULL-AREA, SELECTIVE-SPECTRAL, REMOTE IMAGING AND ANALYSIS DEVICE AND PROCESS

(75) Inventors: Rolf Holger Wolters, Honolulu, HI (US); Joseph Allen Sweat, Honolulu, HI (US); Michael James Deweert, Kailua, HI (US); Robert Benton Seiple, Jr., Kailua, HI (US); David George Shibasaki Walton, Honolulu, HI (US)

(73) Assignee: STI Medical Systems, Inc., Honolulu, HI (US)

( * ) Notice: Subject to any disclaimer, the term of this patent is extended or adjusted under 35 U.S.C. 154(b) by 0 days.

(21) Appl. No.: 10/387,761

(22) Filed: Mar. 12, 2003

(65) Prior Publication Data

US 2003/0158470 A1 Aug. 21, 2003

Related U.S. Application Data

(63) Continuation-in-part of application No. 09/885,267, filed on Sep. 18, 2000.

(51) Int. Cl.[7] .................................................. G06K 9/00
(52) U.S. Cl. ..................... 382/128; 382/128; 600/425
(58) Field of Search ................................ 382/128, 129, 382/130, 131, 132, 133, 134; 356/456; 348/65; 600/300, 313, 321, 342, 420, 424, 425, 442, 451

(56) References Cited

U.S. PATENT DOCUMENTS

| 5,162,990 | A | * | 11/1992 | Odeyale et al. | 382/128 |
|---|---|---|---|---|---|
| 5,398,685 | A | * | 3/1995 | Wilk et al. | 600/437 |
| 5,507,278 | A | * | 4/1996 | Karell | 128/200.23 |
| 5,944,653 | A | * | 8/1999 | Bonnell et al. | 600/109 |
| 5,999,844 | A | * | 12/1999 | Gombrich et al. | 600/476 |
| 6,055,451 | A | * | 4/2000 | Bambot et al. | 600/476 |
| 6,081,740 | A | * | 6/2000 | Gombrich et al. | 600/424 |
| 6,128,525 | A | * | 10/2000 | Zeng et al. | 600/476 |
| 6,174,291 | B1 | * | 1/2001 | McMahon et al. | 600/564 |
| 6,198,532 | B1 | * | 3/2001 | Cabib et al. | 356/456 |
| 6,321,111 | B1 | * | 11/2001 | Perelman et al. | 600/477 |
| 6,332,092 | B1 | * | 12/2001 | Deckert et al. | 600/476 |
| 6,603,552 | B1 | * | 8/2003 | Cline et al. | 356/417 |

\* cited by examiner

Primary Examiner—Jayanti K. Patel
Assistant Examiner—Seyed Azarian
(74) Attorney, Agent, or Firm—Martin E. Hsia

(57) ABSTRACT

The invention provides a device and process for real-time screening of areas that can be identified as suspicious either through image segmentation utilizing image processing techniques or through treatment with an exogenous fluorescent marker that selectively localizes in abnormal areas. If screening detects a suspicious area, then the invention allows acquiring of autofluorescence images at multiple selected narrow differentiating spectral bands so that a "virtual biopsy" can be obtained to differentiate abnormal areas from normal areas based on differentiating portions of autofluorescence spectra. Full spatial information is collected, but autofluorescence data is collected only at the selected narrow spectral bands, avoiding the collection of full spectral data, so that the speed of analysis is increased.

15 Claims, 7 Drawing Sheets

Selected Emission Spectra

Note: Peak heights not to scale

DUAL MODE REAL-TIME SCREENING AND RAPID FULL-AREA, SELECTIVE-SPECTRAL, REMOTE IMAGING AND ANALYSIS DEVICE AND PROCESS

This application is a continuation-in-part of Ser. No. 09/885,267 filed on Sep. 18, 2000.

FIELD OF THE INVENTION

This invention relates to a device and process that provides, in a screening mode, real-time screening and remote imaging, and in an analysis mode, rapid full-area, selective-spectral remote imaging and analysis. More specifically, this invention relates to a device for allowing real-time detection and rapid remote analysis of surfaces with differentiating spectral properties, such as potentially cancerous regions in the cervix, intestine, lungs or other organs.

PRIOR ART

Cancers, especially cancers in the intestine, cervix, lungs, and other hollow organs, need to be detected early for effective treatment. For example, intestinal cancers typically start with polyps, either protruding (pedunculated tubular adenomas) or flat (sessile villous adenomas). These polyps sometimes convert into cancer. Therefore, the detection or removal of polyps by colonoscopy significantly reduces the risk of getting colon cancer. Traditionally, polyps are detected using devices that allow a physician to visually examine the interior of the intestine. However, because of the large interior surface area of the intestine, such examinations need to be carried out at a rapid rate so that the maximum area of the intestine can be examined in a minimum amount of time. Further, the amount of time for such examinations must be minimized in order to minimize the expenses and physical impact of such examinations. It is also more difficult to detect flat polyps (sessile villous adenomas) with such examinations.

Two major types of procedures for intestinal examination are sigmoidoscopy and colonoscopy. In these procedures, a device for viewing the interior of a hollow organ, usually an endoscope, is inserted into the intestine through the anus. The endoscope usually includes input from a light source and includes lenses at the end of a long flexible cable. An imaging bundle of coherently bundled optical fibers is usually provided inside the cable to transmit an image with a resolution determined by the number of fibers in the bundle. The field of view of an endoscope can be 45 to 140 degrees, depending on the lenses selected. Some endoscopes also have a biopsy channel in the cable that allows the examining physician to extract a tissue sample, such as a portion of a polyp, for later analysis, such as by a biopsy (or even to extract an entire polyp). In sigmoidoscopy, the patient is conscious during the examination, and therefore, the time for the examination must be minimized to minimize the patient's discomfort during the procedure. Further, sigmoidoscopy does not screen the entire length of the intestine because a sigmoidoscope does not pass beyond a 120-degree bend in the intestine called the left colic (splenic flexure). In a colonoscopy, the entire length of the intestine can be screened, but the patient must be fully anesthetized, which introduces all the attendant risks of anesthetization. Traditional visual analysis of polyps and other colonic lesions requires training and experience. Because polyps are small, and not all polyps are cancerous, it is helpful to somehow mark pre-cancerous polyps or other abnormal tissues to enhance viewing and detection while screening. It is desirable to reduce the overall number of biopsies because there is an increased risk of morbidity with each additional biopsy.

Fluorescence is a well-known phenomenon in which an excitation light of one wavelength causes a material to emit fluorescent light of a different wavelength. For example, household fluorescent lamps are glass tubes filled with mercury vapor and interiorly coated with phosphor, having electrodes at both ends. When the electrodes are energized with electricity, they emit electrons, which strike the atoms of mercury vapor to cause those atoms to emit ultraviolet light. The ultraviolet light (the excitation light) then strikes the phosphor, which causes the phosphor atoms to emit white light (the fluorescent light). For another example, so-called "black light" is actually ultraviolet light that causes certain materials to emit visible light.

Visible light is considered to have wavelengths of between approximately 400 and approximately 760 nanometers (billionths of a meter, or "nm"). Light having wavelengths shorter than approximately 400 nm is considered to be ultraviolet light by the United States Food and Drug Administration and other countries' regulatory agencies. More specifically, UVA radiation is considered to range from approximately 315 nm to approximately 400 nm, UVB radiation is considered to range from approximately 280 nm to approximately 315 nm, and UVC radiation is considered to range from approximately 100 nm to approximately 280 nm. UVA radiation is sometimes referred to as long wave ultraviolet or "tanning rays." UVB radiation is considered to be more dangerous than UVA and causes damage to genes, and UVC radiation is considered to be even more dangerous than UVB because of its shorter wavelength and higher energy. Thus, the power and allowable time for exposing patients to light having wavelengths of less than 400 nm is restricted. However, there are no such restrictions on exposing patients to visible light.

Although the human eye cannot see light having wavelengths shorter than about 400 nm, some imaging devices, such as certain types of CCDs (charge coupled devices) can detect light down to approximately 360 nm or lower.

It has been discovered that when tissues are excited by a certain excitation light (such as ultraviolet or blue or violet light) the fluorescent light emitted by abnormal tissues has a spectrum (including in the visible range) that differs from the fluorescence spectrum of normal tissues at certain differentiating portions (or bands) of the color spectrum. This is because types and/or amounts of various substances (each having distinctive fluorescence spectra) differ in abnormal tissues from those in normal tissues. This phenomenon of fluorescence due to natural characteristics of the tissues is known as "autofluorescence". The naturally occurring substances in tissues that fluoresce when excited are referred to as "endogenous fluorophores."

Another type of fluorescence that may be utilized in cancer detection is induced fluorescence, that is, fluorescence induced by administration of an exogenous (that is, introduced from outside the patient) fluorescent marker (or exogenous fluorphore) that selectively localizes in abnormal precancerous and cancerous tissues. Thus, the abnormal tissues will fluoresce at a particular marker wavelength (or set of wavelengths) when those tissues are illuminated with an excitation light that causes the exogenous fluorescent marker to fluoresce. An example of an exogenous fluorescent marker is 5-aminolaevullinic acid ("ALA"). ALA induces precancerous and cancerous tissue to preferentially accumulate protoporphyrin IX ("PpIX"). PpIX is a photosensitizer, but clears rapidly from the body, limiting the period of enhanced tissue sensitivity to between 24 and 48 hours. When excited with a marker excitation light having a wavelength of around 400 nm, PpIX emits a marker fluorescent light having a characteristic fluorescence spectrum with peaks centered at approximately 635 and 700 nm. In addition, PpIX occurs naturally in humans and causes few side effects.

The intensity of autofluorescence is fairly weak, relative to induced fluorescence, and can be difficult to detect, requiring a longer time for exposure, much as a photograph in weak light requires a long time exposure. Accordingly, it is desirable to use relatively bright light in the visible range (such as blue or violet light) or in the portion of the UVA range near 400 nm to apply enough excitation light to make autofluorescent light bright enough for rapid acquisition of autofluorescence images. Rapid acquisition of images is desirable to avoid blurring due to patient movement, minimizing time for examination, and for other reasons. It is not practical to use high intensity, long duration ultraviolet light to increase the intensity of autofluorescence because such high intensity, long duration ultraviolet light may damage a patient's tissues. Further, there is often a maximum response of fluorophores to excitation light, so that higher intensity excitation light yields little additional emitted autofluorescent light. Also, ultraviolet light can be used only if regulatory requirements, such as limited exposure doses, can be met. In some cases, shorter-wavelength radiation can enhance the autofluorescence signal. However a shorter wavelength light also may increase the risk of damage to a patient's tissues and may be subject to even more stringent regulatory requirements.

Preferably, when induced fluorescence is used, the marker fluorescent light emitted by the exogenous fluorescent marker is much brighter than the autofluorescence emitted by the tissues to allow for comparatively faster image acquisition, which in turn allows for rapid screening for potentially abnormal (suspicious) tissues.

Prior screening methods using ALA were employed to find potentially cancerous lesions or polyps, and a biopsy was then extracted from the tissue to confirm a diagnosis. However, taking a tissue sample creates a risk of cramping, infection, excessive bleeding or perforation, and may be completely out of the question for certain people, such as hemophiliacs or others with impaired clotting ability or immune systems.

Instead of administering ALA (or other exogenous fluorescent marker), screening can be accomplished by creating video images of tissues in visible light and using image processing techniques to indicate areas of potential interest, as described in more detail below, thus providing automated visual screening with increased accuracy and consistency (as compared with manual visual screening).

Of course, both methods could be combined, by administering ALA (or other exogenous fluorescent marker), illuminating the tissues with a marker excitation light to induce marker fluorescence of the ALA (or other exogenous fluorescent marker), and then applying automated screening to the marker image formed by the marker fluorescence.

The differentiating portions of the autofluorescence spectra of normal and abnormal tissues may be faint, so a substantial amount of time is needed to acquire autofluorescence spectral data for analysis. A disadvantage of spectroscopy of a single point is that areas must be spectrally analyzed point by point to delineate the spatial extent of any abnormal tissue. Further, the differentiating portions of some of the fluorescing spectra may be narrow (such as ALA's spectral peaks), so that high spectral resolution may be needed to resolve those particular differentiating portions. Some of the differentiating portions may not need a high spectral resolution, however.

Standard color cameras employ three broad and overlapping red, green and blue bands. Optical devices which detect radiation in multiple bands not confined to the standard three bands are conventionally classified as either hyperspectral or multispectral devices. A spectral resolution of 10 nm or less, with 20 or more spectral bands, is conventionally called hyperspectral resolution. Multispectral analysis conventionally refers to analysis of multiple spectral bands, which may be contiguous or non-contiguous and of different widths, but conventionally implies non-hyperspectral resolution, that is, resolution that does not reach 10 nm or less.

An article entitled "Endoscopic fluorescence imaging and point spectroscopy system for the detection of gastrointestinal cancers" by Nadeau, V. et al, Journal of Modern Optics, 2002, Volume 49, pages 731–741, incorporated herein by reference, discloses a combined endoscopic fluorescence imaging and point spectroscopy system for detecting gastrointestinal cancers utilizing the fluorescence from PpIX. This Nadeau reference teaches the use of point spectroscopy by measuring the full fluorescence spectrum from a single point by passing an optical fiber down the biopsy channel of an endoscope and placing it in contact with the tissue. In the point spectroscopy mode, the fiber optic abuts against the region of interest and the acquired light is then spectrally analyzed, apparently without forming an image remotely (there is no suggestion that the fiber optic consists of multiple fibers that are coherently bundled so as to be capable of forming images). The spectrometer provides "a signal resolution of 10 nm over the range 350 nm to 850 nm." The area of coverage for point spectroscopy therefore depends on the size of the fiber optic that abuts against the tissue, which may make determination of the extent (i.e., perimeter) of the abnormal tissue difficult.

An article entitled "An endoscopic fluorescence imaging system for simultaneous visual examination and photodetection of cancers" by Wagnieres, G., et al., Rev. Sci. Instrum., Vol. 68, No. 1, January 1997, pages 203–212, incorporated herein by reference, discloses a fluorescence endoscope in which the fluorescence contrast between the tumor and surrounding normal tissue is enhanced by real time image processing by simultaneously recording the fluorescence image in two spectral domains, after which the images are digitized and manipulated with a mathematical operator (look-up table) at video frequency. The device also allows for immediate observation of the endoscopic area under white light illumination during fluorescence detection in order to localize the origin of positive fluorescence signals.

An article entitled "An endoscopic system for the early detection of cancers of the gastrointestinal tract", McKechnie, T., et al., Rev. Sci. Instrum., Vol. 69, No. 6, pages 2521–2523 (June 1998), incorporated herein by reference, discloses a 3-color camera, an intensified CCD camera and an fiber-coupled spectrometer, all of which are simultaneously mounted on a standard endoscope. This device specifically allows the operator to record a full optical spectrum of a particular region of a tissue.

An article entitled "An endoscopic imaging system for the early detection of cancer" by Padgett, M., and Sibbett, W., incorporated herein by reference, discloses the use of ALA as a fluorescent marker with a miniature color camera to provide a navigation image under normal white light illumination and an intensified camera filtered to detect light between 630 and 640 nm, i.e., an image showing only PpIX fluorescence.

U.S. Pat. No. 5,590,660 to MacAulay, et al., incorporated herein by reference, discloses an apparatus employing a light source for producing excitation light to excite the tissue to generate autofluorescence light and also for producing illumination light. A filter acts to integrate the autofluorescence image over a range of wavelengths in which the autofluorescence intensity for normal tissue is substantially different from the autofluorescence intensity for diseased tissue to establish an integrated autofluorescence image of the tissue. A monitor then displays the integrated autofluorescence image and the remittance light image to produce a normalized image in which the diseased tissue is distinguishable from normal tissue.

U.S. Pat. No. 5,507,287 to Palcic, et al., incorporated herein by reference, discloses a light source for generating excitation light that includes wavelengths capable of generating characteristic autofluorescence from abnormal and normal tissue. An imaging bundle collects autofluorescence light from the tissue, which is then filtered into spectral bands by a filter wheel. For one of the spectral bands, the autofluorescence intensity for abnormal tissue is substantially different from normal tissue, while for the other spectral band the autofluorescence intensity for abnormal tissue is substantially similar to that for normal tissue. An optical system intercepts the autofluorescence light to acquire at least two filtered emitted autofluorescence images of the tissue. These acquired images are displayed in real time on a display monitor so as to delineate abnormal and normal tissue. Synchronizing means are disclosed to allow for alternate illumination of the tissue by laser light and a white light source. However, Palcic indicates that one transformation which has been reported with tumor localizing drugs was found not to be useful for the imaging method.

U.S. Pat. No. 6,236,881B1 to Zahler, et al., incorporated herein by reference, discloses a computerized apparatus implementing a real time detection algorithm for non-drug activated imaging of diseases. A metal halide light source produces excitation light to excite the tissue to generate combined reflection and autofluorescence light. An optical system coupled to a digital color and multispectral camera collects the combined reflection and autofluorescence light for the inspected tissues. The system contains a miniature filter wheel, running synchronously with the camera video frame for real time buffering and multitasked spectral and spatial segmentation algorithm implementations.

U.S. Pat. No. 6,160,618 to Garner, incorporated herein by reference, discloses a hyperspectral slide reader in which an imaging spectrometer is positioned in the path of a light from the side to split the light line into a light array, and the camera can detect the entire spectrum of light produced by the imaging spectrometer.

U.S. Pat. No. 5,782,770 to Mooradian, et al., incorporated herein by reference, discloses techniques and devices for diagnosing tissue via hyperspectral imaging in which a 3-dimensional image is formed where two dimensions contain information about an area, and one dimension contains full spectral information for that area. The spectral content of the image can be analyzed on a pixel by pixel basis to determine the presence of certain matter and the spatial extent thereof.

Published Patent Cooperation Treaty International Patent Application PCT/US94/00702 (International Publication No. WO94/16622), incorporated herein by reference, discloses an apparatus that produces a diagnostic image by exposing a live tissue specimen in situ to a primary light, selecting particular wave lengths of secondary light returned from the examined tissue, and obtaining one or more sequential images from the examined tissue.

U.S. Pat. No. 5,379,065 to Cutts, incorporated herein by reference, discloses a hyperspectral imager including a focal plane having an array of spaced image recording pixels, an electronic shutter and an electronic spectral filter for selecting a spectral band of light received by the focal plane and an electronic controller, controlling the rate at which a recording is transported in the longitudinal direction, the exposure time and the spectral bands so as to record a selected portion of the scene through M spectral bands with a respective exposure time $t_q$ for each respective band q.

U.S. Pat. No. 5,413,108 to Alfano, incorporated herein by reference, discloses a method and apparatus for examining a 2-dimensional region of a tissue sample by exciting the tissue sample with light at a first wavelength and measuring the resultant fluorescence at an emission wavelength. The two-dimensional region is then illuminated again at a second wavelength, and the resultant fluorescence is measured at the same emission wavelength. The two wavelengths are chosen so that the ratio or difference of fluorescence intensities at the emission wavelength is indicative of the carcinomatous condition of the tissue.

DISCLOSURE OF INVENTION

The process of this invention comprises providing an area that contains both normal and abnormal tissues with an exogenous fluorescent marker that selectively localizes in abnormal tissue and that fluoresces (preferably brightly) at a particular marker wavelength when illuminated by an excitation light. Imaging light (preferably white visible light) is then filtered to remove light of that marker wavelength to result in markerless imaging light. Of course, alternative means for creating markerless imaging light can also be used, such as using multiple broadband light sources that do not emit light at the marker wavelength, one emitting light at shorter wavelengths and the other emitting light at longer wavelengths. In a screening mode, the area is illuminated with both markerless imaging light and an excitation light, so that the exogenous fluorescent marker in the abnormal tissue is induced to fluoresce (preferably brightly enough that the fluorescent light can be detected even though the tissues are simultaneously illuminated with an imaging light) at the marker wavelength. Light at the marker wavelength is then separated to form a marker image, while the remaining light forms a background image, over which the marker image is preferably overlaid, displayed side by side, or displayed alternately. The user can thus rapidly scan for areas of potential interest (suspicious areas), avoiding the delay of analyzing areas that do not fluoresce at the marker wavelength.

Instead of using a fluorescent marker, screening can be performed automatically by creating a video image of the tissues in visible light using the imaging light (optionally including ultraviolet light down to approximately 360 nm) and then using image processing techniques to indicate areas of potential interest (pre-segment the scene) in preparation for the analysis mode, as described below. Of course, if this automatic screening using image processing of visible light images is used, without administration of ALA (or other exogenous fluorescent marker), then there is no need for a marker filter. This automatic screening using image processing techniques can also be combined with the use of an exogenous fluorescent marker. Screening can also be performed with conventional visual examination.

If an area of potential interest (suspicious area) is found during the screening mode (either by automatic image processing of a visible light image to pre-segment the scene, or by fluorescing at the marker wavelength, or conventional visual examination), the user can activate an analysis mode (a "virtual biopsy") in which that area is illuminated only with the (preferably ultraviolet) excitation light, and the resulting autofluorescence light is remotely imaged at multiple narrow spectral bands selected to differentiate normal from abnormal tissues (and optionally a reference band for normalization), so that full area images at selected spectral bands are formed, whereby collecting full spectral information is avoided. This is referred to as "full-area, selective-spectral" imaging. Preferably, the resolution of at least one of the selected spectral bands is 10 nm or less, but this is not necessarily always the case. Preferably at least some of the selected bands are non-contiguous, but surprisingly, as noted below, contiguous or overlapping bands may be preferred if they discriminate efficiently between normal and abnormal tissues. These full-area, selective-spectral images can then be analyzed to differentiate the abnormal tissue from normal tissue, thus constituting a selective-spectral analysis.

Because only selected portions of the autofluorescence spectrum are collected, collection of the remaining portions of the autofluorescence spectrum is avoided, so that the process is much faster than prior art processes, which take the time to collect full spectral data, and then discard unused portions. Avoiding the collection of spectral data unnecessary or superfluous for differentiating normal from abnormal tissues allows for rapid acquisition of the autofluorescence spectral data that is necessary for such differentiation and hence for rapid analysis, that is, analysis in near real time, or approximately in real time. The term "real time" refers to a time brief enough that it is easily incorporated into the examination sequence, such as less than approximately 5 seconds per scan or analysis. The terms "near-real time" or "approximately in real time" or "approximate real time" or "rapid" refer to time spans short enough that multiple analyses are available quickly enough to be usable within the time of a typical medical examination, such as less than approximately 30 seconds per analysis.

Because it is not necessary to contact the tissue in either mode, the process allows remote imaging and analysis.

The device of the invention is a device that includes an imaging light source emitting imaging light and an excitation light source emitting excitation light. Preferably, a user-activatable shutter (or other means to regulate light output) is provided to selectively block the imaging light. The user thus controls what mode is employed. Alternatively, either or both of the imaging light source and excitation light source can be light emitting diodes or LEDs (preferably temperature stabilized to preserve spectral purity by avoiding spectral fluctuations caused by warming up and cooling down) with power that is switched or cycled on or off as modes are changed by the user, which eliminates a mechanically moving part.

Of course, either or both of the imaging light source and excitation light source can also be any other kind of light, such as a lamp, including an arc lamp, quartz-halogen lamp, or other lamp, or laser. The imaging light is preferably white visible light with an approximately flat spectral output from approximately 360 nm to approximately 760 nm, and the excitation light is preferably selected from either blue or violet light or ultraviolet light. An optical combiner, such as a dichroic mirror (a mirror that passes some wavelengths and reflects others), then combines the imaging light (when turned on or when not blocked by the shutter) and the excitation light. Of course, the optical combiner can be separate fiber optic bundles for the markerless imaging light and for the excitation light that are combined in the light guide, or other alternatives, as well. Optionally, if a fluorescent marker will be used, a narrow band filter (marker filter) removes light at a marker wavelength from the imaging light, resulting in markerless imaging light. A light guide then directs the markerless imaging light and the excitation light onto the tissue so that the tissue is selectively illuminated with either (in an analysis mode) the excitation light alone (the imaging light is turned off or blocked by the shutter), or (in a screening mode) both the excitation light and the markerless imaging light (the imaging light is turned on or is not blocked by the shutter). Of course, other alternatives for selectively illuminating the tissues with the excitation light and/or the markerless imaging light can be used.

If an exogenous fluorescent marker has been previously administered (such as by injection, ingestion, or otherwise), during the screening mode, the excitation light induces abnormal tissue to fluoresce brightly enough at the marker wavelength to be visible when the tissue is simultaneously illuminated with markerless imaging light. During the analysis mode, the abnormal tissue autofluoresces differently from the normal tissue at differentiating portions of the tissue's fluorescent spectrum.

An imaging bundle is positioned to transmit an image of the tissue as it autofluoresces during the analysis mode, preferably starting at a wavelength just above the wavelength of the excitation light, such as (for example) 360 nm. Of course, the imaging bundle also transmits an image of the tissue as it is illuminated by the imaging light (and simultaneously by the excitation light if induced fluorescence is being used) during the screening mode. An adjustable narrow band filter is operably connected to the imaging bundle that:

in a screening mode (with the shutter open or the imaging light on), directs fluorescent light at the marker wavelength emitted from the tissues to a sensitive (preferably) monochromatic imaging device (such as a CCD, CMOS, or equivalent) to form a marker image, and that directs reflected light from the tissues to a color or black and white, preferably high resolution, imaging device (such as a color CCD, CMOS, or equivalent) to form an imaging image; and in an analysis mode (with the shutter blocking the imaging light or the imaging light off), deflects only multiple selected (preferably narrow) bands of the differentiating portions of the autofluorescence spectrum (and optionally a reference band) to the monochromatic imaging device to form multiple selective-spectral images.

An image processor is then operably connected to the imaging devices that combines data from the imaging devices in approximately real time that:

in the screening mode, creates a false color overlay of the marker image from the monochromatic imaging device over the imaging light image from the high resolution imaging device; and in the analysis mode, analyzes multiple selected (preferably narrow) bands of differentiating portions (and optionally a reference band) of the autofluorescence spectrum and differentiates the normal tissue from the abnormal tissue to create a differentiated image of the abnormal tissue. The image processor can be operably connected to a display device, such as a monitor, and the differentiated image of the abnormal tissue can be displayed over the imaging light image from the high resolution imaging device. Optionally, the selected spectral bands of the differentiating portions can be displayed in selected false colors to enhance visual detection of abnormal tissue. Of course, instead of overlaying the images, other means for visual comparison can be used, such as displaying the images side by side display, or alternating images.

Thus, in the screening mode, the tissue is illuminated by both the imaging light and the excitation light, but in the analysis mode, the tissue is illuminated only by the excitation light. Alternatively, if automated visual screening is performed by pre-segmenting the scene using image processing, the tissue is illuminated only with imaging light during the screening mode, and only by the excitation light during the analysis mode.

The device combines the speed of screening using an exogenous fluorescent marker (or pre-segmenting the scene using image processing) with (when the user selects) the ease and accuracy of using spectral analysis to confirm that a suspicious area is cancerous (thus avoiding the need for a biopsy). Further, because the device avoids collecting unnecessary or superfluous spectral data during the analysis mode, the analysis can be performed rapidly, in near real time or approximately in real time.

The imaging of both imaging devices preferably preserves all spatial information, such as shape and texture. The imaging devices can be operably connected to display devices, such as monitors, to display full-area images of the tissues in both modes.

It is preferred that the imaging light extend to ultraviolet wavelengths overlapping the excitation light spectrum (or the shortest wavelength of autofluorescence) so that at least a portion of the resulting imaging image is collected at the same wavelengths as the autofluorescence image. This allows both the imaging image and the autofluorescence image to be co-registered, that is, accurately aligned with each other.

With the above invention, a process and device are provided that allow for rapid remote screening, using ALA (or other exogenous fluorescent marker) to indicate the location of potentially abnormal (suspicious) tissue while screening. This screening mode allows real time or near real time screening of large areas of tissue by illuminating the tissue with both markerless imaging light and excitation light, which stimulates emissions at a marker wavelength or wavelengths. In the optical system described above, the excitation light causes the exogenous fluorescent marker to fluoresce at the marker wavelength(s) to form a marker image and the markerless imaging light reflects off the tissues to form an imaging image. The term "marker image" denotes the image formed using the marker fluorescent light emitted by the tissues, preferably displayed on a sensitive monochromatic imaging device. The term "imaging image" denotes the image formed by the markerless imaging light reflected from the tissues, preferably displayed on a high-resolution color (or other multiple chromatic) imaging device. The marker image can be overlaid on the imaging image (or displayed side by side or alternated) to show areas of potential interest (suspicious area).

Alternatively, automatic screening can be accomplished by scene segmentation using image processing techniques, such as fractal pattern recognition in the spatial domain (classifying or segmenting a scene by image characteristics such as granularity or degree of border irregularity), classifying or segmenting a scene by morphology, classifying by the shapes of regions, texture or color, and other image processing methods now known or later developed. With this automatic screening by scene segmentation, only the high-resolution imaging device need be used during the screening mode because the screening can be performed using the full spectral range of the imaging image. However, if scene segmentation can be more efficiently or effectively conducted over specific spectral range(s), then the adjustable narrow band filter can divert a selected spectral band or bands to the monochromatic imaging device during the screening mode as well as during the analysis mode.

If screening is accomplished using ALA (or another exogenous fluorophore), it would be preferred to have two excitation lights, a marker excitation light emitting light (referred to as marker excitation light) at the optimal excitation wavelength for the exogenous fluorophore during the screening mode, and an autofluorescence excitation light emitting light (referred to as autofluorescence excitation light) at the optimal excitation wavelength for stimulating autofluorescence during the analysis mode. Of course, two shutters could then be provided, so that during the screening mode, an autofluorescence shutter blocks the autofluorescence excitation light and the tissue is illuminated only with marker excitation light and the imaging light, and during the analysis mode, a marker shutter blocks the marker excitation light (and the imaging light has been blocked as well) and the tissue is illuminated only with autofluorescence excitation light. Of course, if the excitation lights are cycled between modes by having their power turned on or off, then no shutters would be necessary. Alternatively, some or all of the shutters could also be combined into one shutter with aperture(s) that alternate between the excitation lights (and the imaging light).

If the screening mode finds an area of potential interest (suspicious area), the device can change to analysis mode and illuminate the tissue only with excitation light and then analyze only the differentiating portions of the autofluorescence spectra of the tissues (and optionally a reference band) according to well-known characteristics, such as ratio of spectral peaks, intensities, etc. Other analysis methods, such as fractal pattern recognition in the spatial domain, morphology analysis, and other modes that are developed in the future, also can be used. Preferably, the analysis mode is accomplished through rapid cycling through multiple selected spectral bands. Preferably the spectral bands can be selected to be non-contiguous, contiguous or overlapping. This analysis is fast enough for approximately real time spectral analysis, although enough time must be allowed to acquire and integrate multiple bands of autofluorescence signals, which are weaker than the induced fluorescent signals used in the screening mode.

Area imaging and a sensitive imaging device (such as a CCD) are used to rapidly acquire high-resolution images to allow rapid, almost real time analysis. This invention thus avoids the need for actual biopsies, reducing pain, cost and the risk of infection. Greater optical throughput, decreased image capture time, and reduced blurring (or lost data) from the patient's movements are achieved. This is by contrast to "pushbroom" imaging, in which full spectral data sets are collected and then filtered (which sometimes results in collecting and discarding substantial amounts of unneeded data). Pushbroom imaging also entails a substantial possibility of blurring due to patient movements.

For example, in the present invention, if 5 spectral bands, starting at a wavelength just above the excitation light wavelength or longer (such as starting at 360 nm or longer), each band being approximately 10 to 20 nm wide, are selected for analysis (to determine the differentiating portions of the spectra between normal and abnormal tissues), then approximately 50 to 100 nm of spectral data would be collected in total. Because the full visual spectrum spans approximately 360 nm (400–760 nm), collecting only approximately 50 to 100 nm of spectral data would mean collecting only about one-eighth to about one quarter of the full visible-light fluorescence spectrum available. However, because these bands would be selected to determine the differentiating portions of spectra between normal and abnormal tissue, collecting data only from these bands would be sufficient to differentiate between normal and abnormal tissue. This would mean therefore that collecting the necessary spectral data for analysis would only take approximately one-fourth to one-eighth of the time (or would be 4 to 8 times faster) than collecting the full spectral data, as would be done with conventional pushbroom scanning. Collecting spectral data 4 to 8 times faster would proportionately reduce the examination times and blurring, as compared to pushbroom or other technologies that collect full spectral data.

Moreover, if the excitation light is ultraviolet, patients are exposed to less ultraviolet light because examination times are reduced. In addition, because ALA induces accumulation of the photosensitizer PpIX (or another photosensitizer may have been administered to the patient), collecting spectral data faster by using selective spectral (instead of full spectral) imaging may be desirable.

Further, because full spatial imaging of autofluorescence is performed, with preferably the same field of view as the visual light imaging, the spatial extent of abnormal tissue can be determined in the analysis mode, as opposed to point spectroscopy, which would require point by point examination to determine the boundaries of the abnormal tissue, which would be much slower, and may miss points.

With this invention, full spatial data and only selected spectral data are collected, because only the differentiating portions necessary for spectral analysis are collected. Thus, "pushbroom" imaging is like older low-speed photocopiers, scanners and fax machines, while full-area imaging is like modern high-speed photocopiers, and is made even faster by collecting only the selected spectral data necessary to differentiate normal from abnormal tissues. This makes analysis faster, reducing patient movement, discomfort and blurring.

If a polarizing filter is used in this system, analysis speed can also be increased. A polarizing filter (such as an acousto-optical tunable filter (AOTF) or liquid crystal tunable filter (LCTF) or other filter that uses polarization) both diverts (diffracts) and transmits separate portions (usually approximately half each) of the light that is inputted, based on the polarization. The transmitted light portion can be separated and used to increase the diverted signal in several ways, such as by changing the polarization of the light that would be transmitted to match the polarization of the light that would be diverted (using means known to those skilled in the art, or other device now known or later invented) before it passes through the filter, and then recombining the light, or other means known to those skilled in the art. With increased optical throughput, the time for analysis of autofluorescence is correspondingly decreased.

BEST MODE FOR CARRYING OUT INVENTION

While this invention is illustrated and described with respect to a presently preferred best mode with respect to screening and analysis of the intestine, devices according to this invention may be in many different configurations, forms, and materials, and applied to screening and analysis of other tissues, organs, materials and objects. The best mode disclosed herein is an exemplification of the principles of the invention and the associated functional specifications of the materials for its construction, and is not intended to limit the invention to the illustrated best mode. Those persons skilled in the art will envision many other possible variations within the scope of the present invention.

Figure 1:
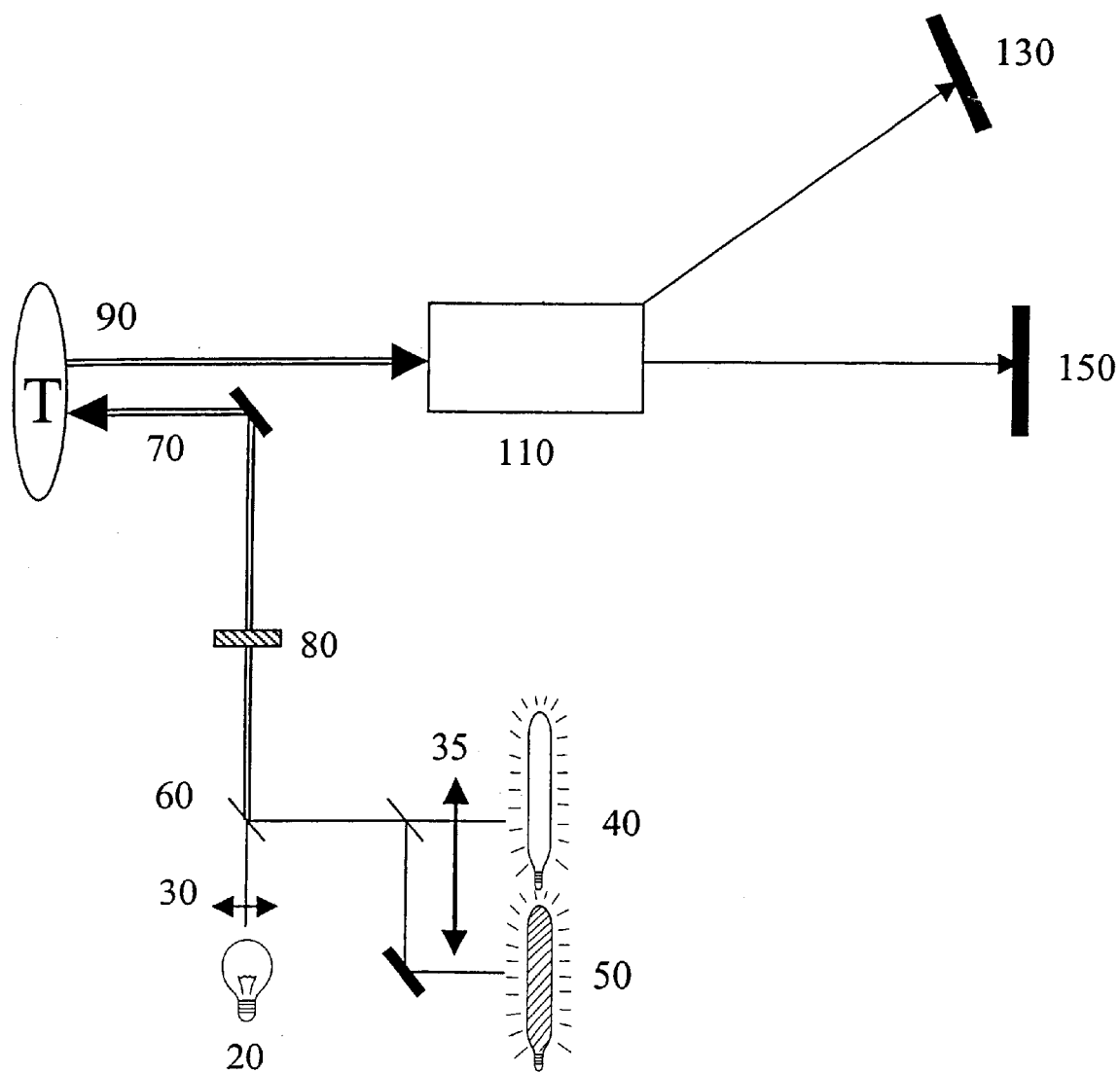
FIG. 1 is a schematic view of a presently preferred embodiment of a device according to the present invention.

The presently preferred best mode for carrying out the present invention is illustrated by way of example in FIG. 1.

Referring to FIG. 1, the device includes an imaging light source 20 preferably emitting approximately spectrally flat broadband visible white light from UVA wavelengths (or the shortest autofluorescence wavelength) through all wavelengths in the visible range, such as a quartz-tungsten halogen bulb or phosphor-coated light emitting diode ("LED"). Also provided is a marker excitation light 40, preferably a narrow wavelength light (such as a blue or ultraviolet LED) preferably emitting blue or violet light (to coincide with the absorption maximum that induces greatest emission by ALA or other exogenous fluorophor). Preferably, an autofluorescence excitation light 50 is also provided emitting narrowband UVA light between approximately 330 nm to approximately 350 nm, to provide excitation light for autofluorescence in an analysis mode. These two sets of excitation lights are preferably provided because ALA (or other exogenous fluorescent marker) and endogenous fluorophores have different optimal absorption peaks (approximately 405 nm for ALA and an empirically determined approximately 330 nm to approximately 350 nm for endogenous fluorophores) that lead to the greatest emission at characteristic emission frequencies. Preferably these two sets of excitation lights are correspondingly alternated as the device is alternated between screening mode or analysis mode, so that the same optics can be used. This alternating of the two sets of excitation lights can be accomplished by, for example, shutter(s) 35, either a separate shutter for each excitation light or a single shutter for both, but with an aperture for only one excitation light at a time. It is believed that the presence of ALA does not affect the autofluorescence spectra of the endogenous fluorophores. The light from the imaging light 20 and the excitation light 40 or 50 (depending on mode) is preferably combined by an optical combiner 60, preferably a dichroic mirror, which transmits visible light and reflects blue or ultraviolet light. The combined light is transmitted by an illuminating light guide 70. An imaging light shutter 30 is preferably provided between the imaging light source 20 and the optical combiner 60, to selectively block the imaging light source 20 so that illumination can be provided either solely by the imaging light source 20 and the marker excitation light 40, or solely by the autofluorescence excitation light 50. A notch filter 80 is provided to remove light at a fluorescent marker band, such as 640 nm, from the imaging light to form markerless imaging light. The illuminating light guide 70 (preferably part of an imaging endoscope or colonoscope and with ultraviolet transmissive illumination fiber optics) then guides the markerless imaging light and the excitation light to illuminate the tissues T. Thus, the tissues T can be selectively illuminated either by both imaging light 20 and marker excitation light 40, or, through activation of the imaging light shutter 30 and cycling (or blocking by shutter (s) 35) of the marker excitation light 40, only by the autofluorescence excitation light 50.

If the tissues T have been previously treated with an exogenous fluorescent marker that preferably localizes in abnormal tissue, in the screening mode, the abnormal tissue will be illuminated by both markerless visible light and maker excitation light and will fluoresce at the marker wavelength (of course, both the normal and abnormal tissue will reflect the markerless visible light as well). In the analysis mode, abnormal tissue will autofluoresce differently from the normal tissue at differentiating portions of the tissue's autofluorescence spectrum.

In either mode, an imaging bundle 90, preferably bundled with the illuminating light guide 70, transmits an image of the tissue T as illuminated. Preferably the imaging bundle is in a commercially available imaging fiber-optic endoscope or colonoscope, with a field of view typically ranging from 90 to 140 degrees. The fibers of the illuminating light guide 70 must have "ultraviolet transmissivity", that is, sufficient transmissivity of ultraviolet light to allow illumination of the tissues by excitation lights 40 and 50 to cause the tissues to fluoresce strongly enough for real time or near real time analysis in the scanning mode and near real time analysis in the analysis mode. Operably, ultraviolet transmissivity should be at least 10% of UVA light, that is, the fibers should transmit at least 10% of UVA light. Preferably, ultraviolet transmissivity should be at least 80% of UVA light. Optimally, ultraviolet transmissivity should be at least 90% of UVA light. Preferably, at least some of those fibers are preferably fused-silica-core fibers transmitting approximately 95% of ultraviolet light between approximately 330 nm and approximately 400 nm.

An adjustable narrow band filter 110 receives the image from the imaging bundle. Preferably the adjustable narrow band filter is an acousto-optical tunable filter, liquid-crystal tunable filter, filter wheel or other device that can be adjusted to allow selected narrow spectral bands to be separated. Optionally, the adjustable narrow band filter also can select broad spectral bands Preferably the adjustable narrow band filter collects spectral information from 4 to 9 spectral bands at the highest frequency possible consistent with acquiring a usable signal, preferably less than one second for each band. The wavelengths and bands selected for analysis would preferably be chosen based on the types of abnormal tissue of interest and discriminatory ability between various spectra.

Figure 2:
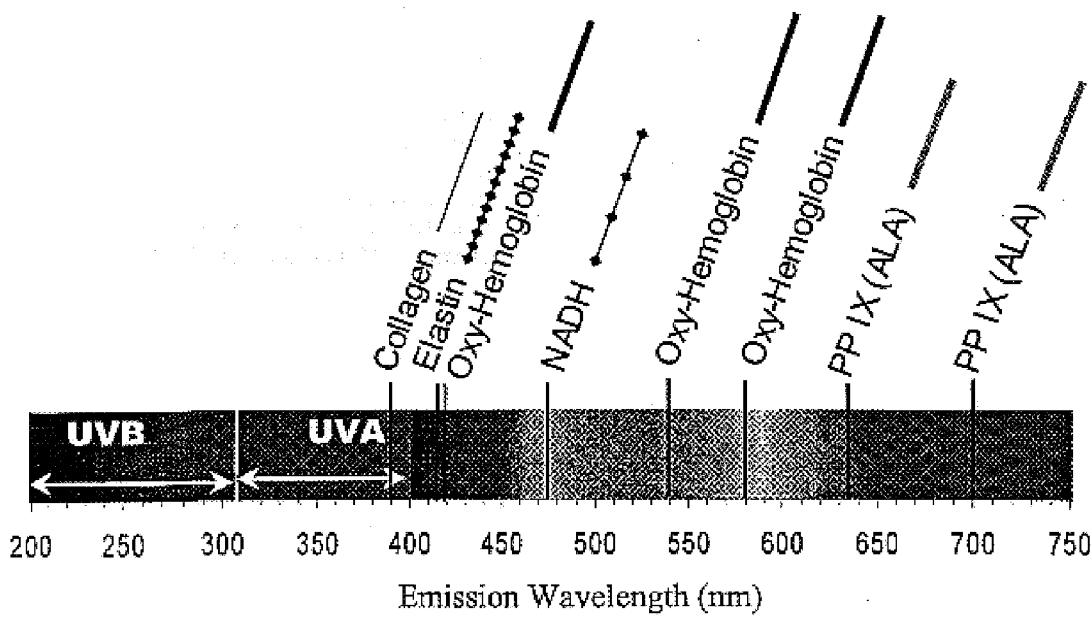
FIG. 2 is a diagram of selected emission spectra for various substances.
Figure 2:
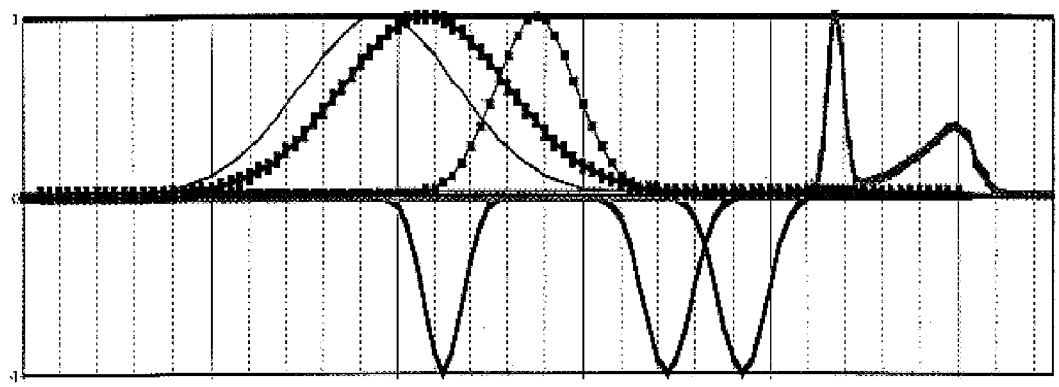

For example, referring to FIG. 2, nicotinamide adenine dinucleotide dehydrogenase (NADH) has a spectral emission peak having a full width of about 50 nm at half of its maximum intensity (50 nm full width, half maximum), centered at approximately 475 nm. For a further example, collagen has a 100 nm full width, half maximum, spectral peak, centered at approximately 390 nm, which extends well into the visible range starting at 400 nm. Elastin has a 100 nm full width, half maximum, spectral peak, centered at approximately 415 nm. Usefully, oxyhemoglobin has spectral reabsorption features centered at approximately 422 nm, 542 nm and 580 nm (40 nm full width, half maximum). As can be seen, PpIX (produced in response to ALA) has a 10 nm full width, half maximum peak centered at approximately 635 nm, and a second 50 nm full width, half maximum peak centered at approximately 700 nm. However, the peak for tryptophan is centered at approximately 340 nm, which is in the ultraviolet.

It would be preferred to have a spectral band that remains unchanged between normal and abnormal tissue to normalize the imaging data (that is, adjust the signal strength ratios between types of tissues), and this can be provided by, for example, flavin adenine dinucleotide (FAD). With this band, the ratios between the peaks of interest in the normal and abnormal tissues can be compared to a basic reference value in order to accurately calculate ratios of changes or perform other analyses.

Surprisingly, the most efficient spectral bands to select for differentiating between various substances may not be solely multiple non-contiguous narrow spectral bands. For example, the most efficient spectral bands to select for rapidly analyzing the differentiating portions of the spectra of certain substances (especially when considering computation time that may be necessary for analysis) may actually be one or more narrow spectral bands, at least one of which overlaps or is adjacent to a broad or intermediate spectral band, or even multiple overlapping or adjacent broad spectral bands. For example, human color vision evolved into cones with overlapping red and green spectral bands, which may be efficient for analyzing spectral properties of natural scenes for tasks such as differentiating ripe fruit from unripe fruit. See "Color Opponency is an Efficient Representation of Spectral Properties in Natural Scenes", Lee, T., et al., Vision Research 42, 2095–2103 (2002); "The Evolution and Physiology of Human Color Vision: Insights from Molecular Genetic Studies of Visual Pigments" by Nathans, J., Neuron, Vol. 24, 299–312, October 1999; "Vision and Signals On Coral Reefs: Can Nature's Technology Help Improve Remote Sensing?", Marshall, J. et al., Proceedings of the SPIE: Ocean Optics XVI, Bellingham, Wash. (2002), all of which are hereby incorporated herein by reference. However, it would be expected that selecting multiple non-contiguous narrow spectral bands would be most effective for certain other substances. Thus, it is preferred that the adjustable narrow band filter be adjustable to filter narrow, intermediate and broad spectral bands, and optionally also be able to filter overlapping or adjacent narrow, intermediate or broad spectral bands, so that the width and frequencies of the spectral bands can be selected to maximize efficiency of analysis of the differentiating portions of the spectra of the particular substances of interest.

Once data at selected spectral bands is collected, it can be analyzed by standard methods to differentiate normal tissue from abnormal tissue in many ways known to persons having ordinary skill in the art. For example, the ratios of spectral peaks at selected spectral bands can be used to delineate various areas of tissue. Other possible methods include principal component analysis, minimum noise fraction, wavelet analysis, band ratio test or any combination of multiple algorithms, including the algorithms described in U.S. Pat. No. 5,413,108, 6,208,749, 6,081,612, 5,697,373, 5,842,995, 5,303,026, 5,991,028, 5,598,481, 5,666,434, 5,673,332, 5,740,268, all of which are incorporated herein by reference. Other methods could include fractal pattern recognition in the spectrum, as described in the U.S. provisional patent application filed on Nov. 13, 2002, Ser. No 60/425659, entitled "Fractal-Based Method for Discriminating Tissue Classes in Medical Images" by Michael James DeWeert, incorporated herein by reference, as well as other methods that may be developed in the future.

In a screening mode, the shutter 30 is open, tissues T are illuminated with both the marker excitation light 40 and markerless imaging light. The tissues T reflect the markerless imaging light and also emit fluorescent light at the marker wavelength. The adjustable narrow band filter 110 directs light at the marker wavelength, such as approximately 640 nm for ALA, to a monochromatic CCD 130 to form a marker image, and all remaining light to a high resolution color CCD 150 to form an imaging image. The marker image and the imaging image can be displayed side by side, overlaid, alternately displayed, or otherwise displayed to allow the user to screen for suspicious areas.

Alternatively, the screening mode can be implemented using only an imaging light (without an exogenous fluorescent marker) by illuminating the tissues T only with the imaging light so that the tissues reflect the imaging light. The adjustable narrow band filter then directs the imaging light to the high resolution CCD 150 to form an imaging image, and image processing is performed on the imaging image to identify suspicious areas, as described below.

If a suspicious area is found, whether by the screening mode, conventional visual examination in visible light, or otherwise, the device can be changed to an analysis mode. In the analysis mode, the shutter 30 is closed, tissues T are illuminated only with the autofluorescence excitation light 50, and multiple narrow spectral bands (at least some selected to be within the differentiating portions of the fluorescence spectrum between normal and abnormal tissues) are diverted by the adjustable narrow band filter 110 to the monochromatic CCD 130. Preferably the monochromatic CCD synchronously cycles with the adjustable selected narrow band filter through the multiple selected narrow spectral bands so that the sensitive monochromatic CCD 130 collects spectral information for a full image at each of the multiple selected narrow spectral bands. If, for example, a filter wheel is used for the adjustable narrow band filter, the monochromatic CCD would collect, first, an image in a first narrow spectral band, then a second separate image in a second narrow spectral band, then a third separate image in a third narrow spectral band, and so on. The various separate images ("selective-spectral images") collected by the monochromatic CCD in the analysis mode can then be manipulated by image processing software, which is well within the skill of a person with ordinary skill in the art, to identify areas of the tissues T in which the ratio of spectral peaks, or the relative intensities of spectral peaks, or other differentiating characteristics (within the differentiating portions of the spectrum between normal and abnormal tissue), can be used to delineate the areas of the tissues T that are abnormal. As described above, optionally one of the selective-spectral images can be used for normalizing data. This results in a "virtual biopsy" by which the entire imaged area can be spectrally analyzed to differentiate abnormal tissue from normal tissue and, optionally, to display a differentiated image with areas of abnormal tissue delineated. The differentiated image can be displayed side by side with the imaging image, displayed overlaid on the imaging image, alternated with the imaging image, or otherwise displayed for use.

This is a selective-spectral analysis, in which spectral information from a full image of fluorescing tissue is collected at multiple selected narrow spectral bands (with at least one of the bands within the differentiating portions of the fluorescence spectra for normal and abnormal tissues) and then the resulting selective-spectral images are analyzed by using differentiating characteristics of those differentiating portions to delineate abnormal areas of tissue. The analysis mode can be conducted in near real time ("approximately in real time") because only information about multiple selected narrow spectral bands is collected (at least one of which is within the differentiating portions), thus avoiding the delay of collecting full spectral information and then discarding the spectral information that is unnecessary to differentiate between normal and abnormal tissue (or to normalize the information between bands).

Of course, the various selective-spectral images can be individually displayed or displayed in one or more groups using various corresponding colors to form false color images. These false color images can make it much easier to distinguish abnormal tissue from normal tissue for analysis and diagnosis. For example, certain spectral bands can be displayed with selected corresponding colors, at chosen relative intensities, so that the coloring, shading and contrast of the resulting false color images can be helpful in diagnosis and analysis.

If the adjustable narrow band filter is an acousto-optical tunable filter or other polarization sensitive filter (collectively, "AOTF"), such as tellurium dioxide or quartz (silicon dioxide), the AOTF will only divert (refract) inputted light of one polarization, and light that is not of the correct polarization will not be diverted. Optical designs known to those skilled in the art can be employed to use the portions that would be rejected by a single AOTF.

Figure 3:
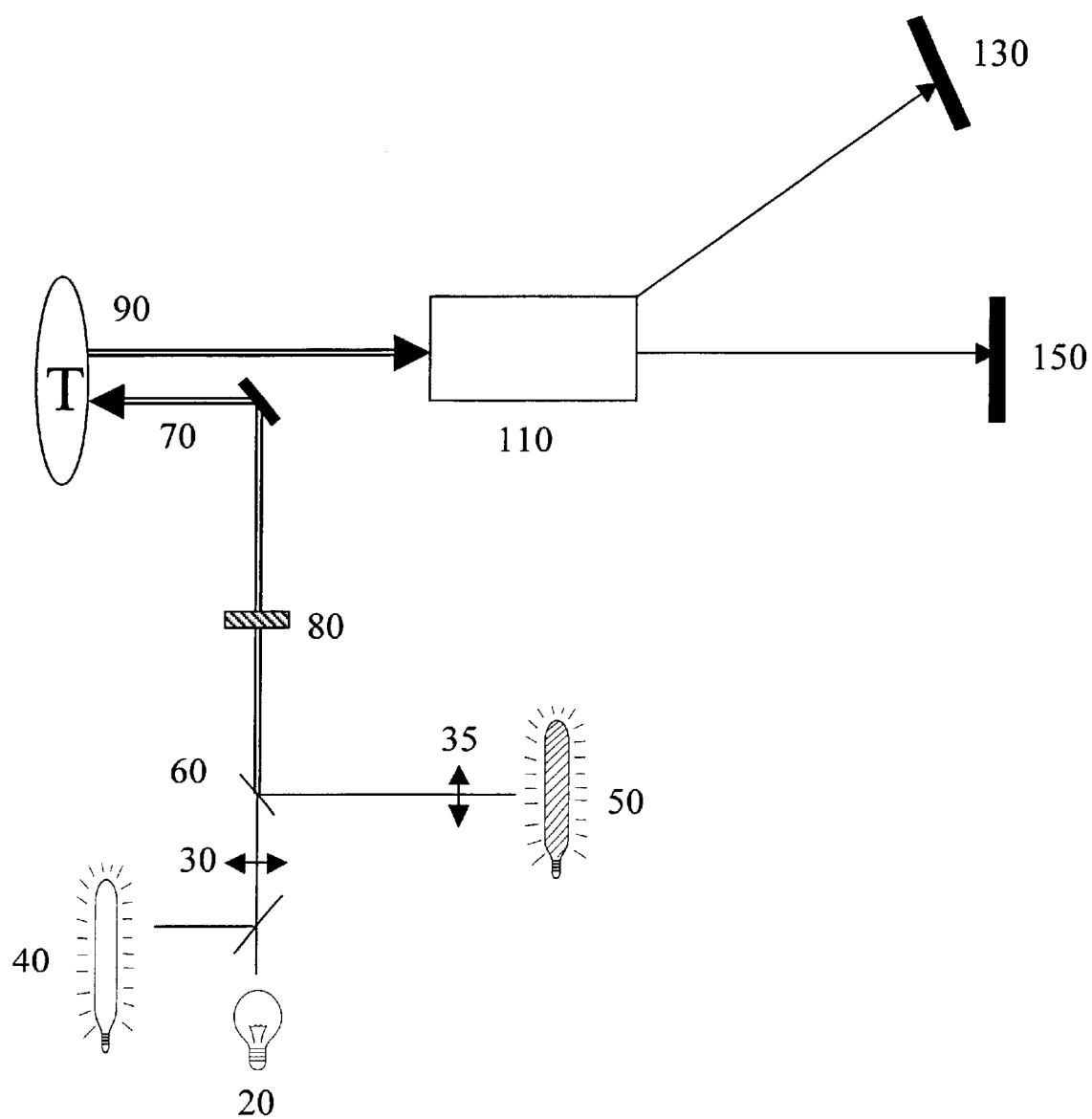
FIG. 3 is a schematic view of an alternative embodiment of a device according to the present invention using an alternative lighting configuration.

FIG. 3 shows an alternative configuration of the imaging light 20 and marker excitation light 40 and autofluorescence excitation light 50, in which the imaging light 20 and the marker excitation light 40 are controlled by a single shutter 30.

Figure 4:
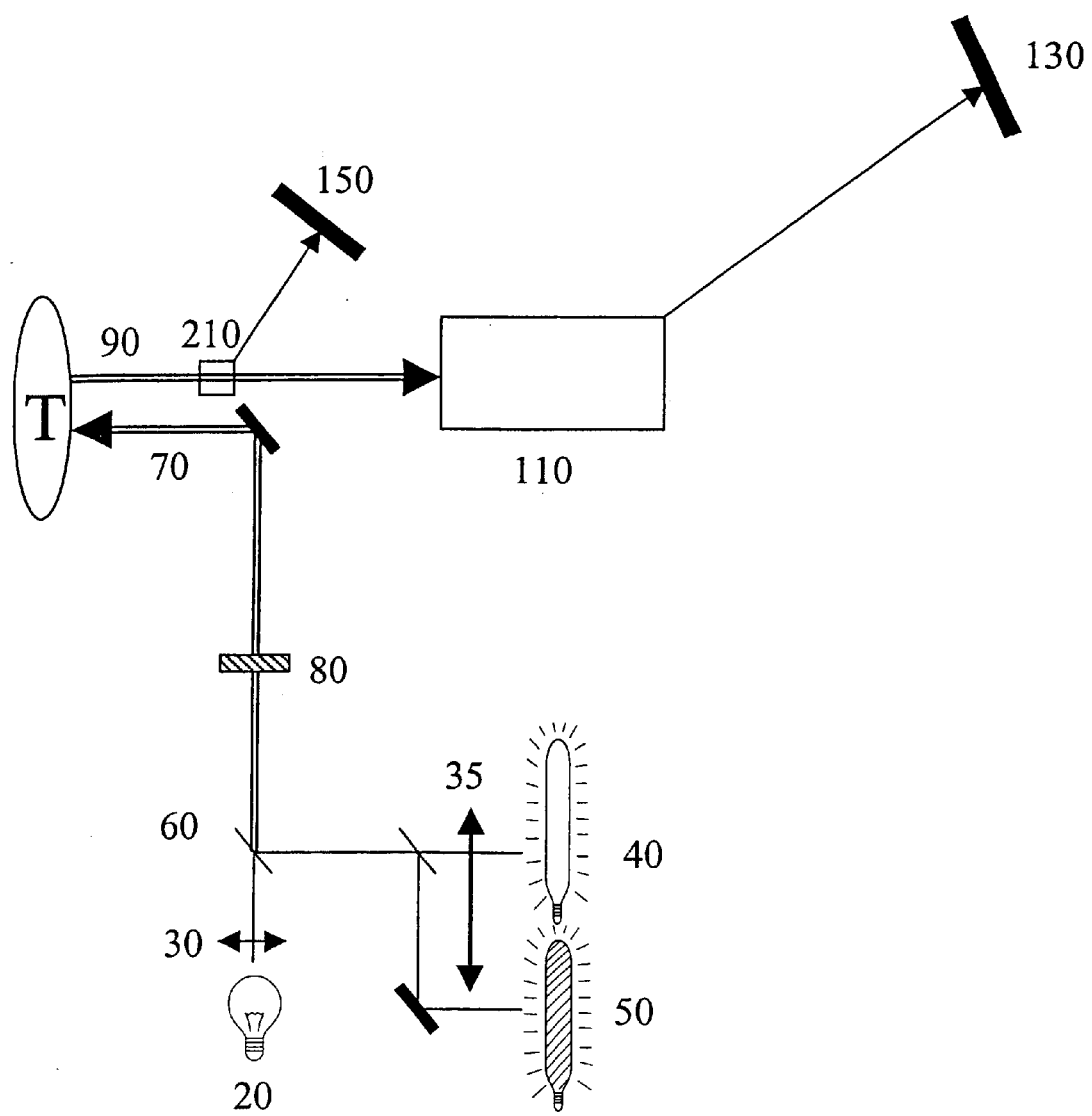
FIG. 4 is a schematic view of an alternative embodiment of a device according to the present invention using a polarization beam splitter to send an image directly to a high resolution imager.

FIG. 4 shows another alternative embodiment in which a polarization beam splitter 210 separates and sends light directly to a high resolution CCD 150.

Figure 5:
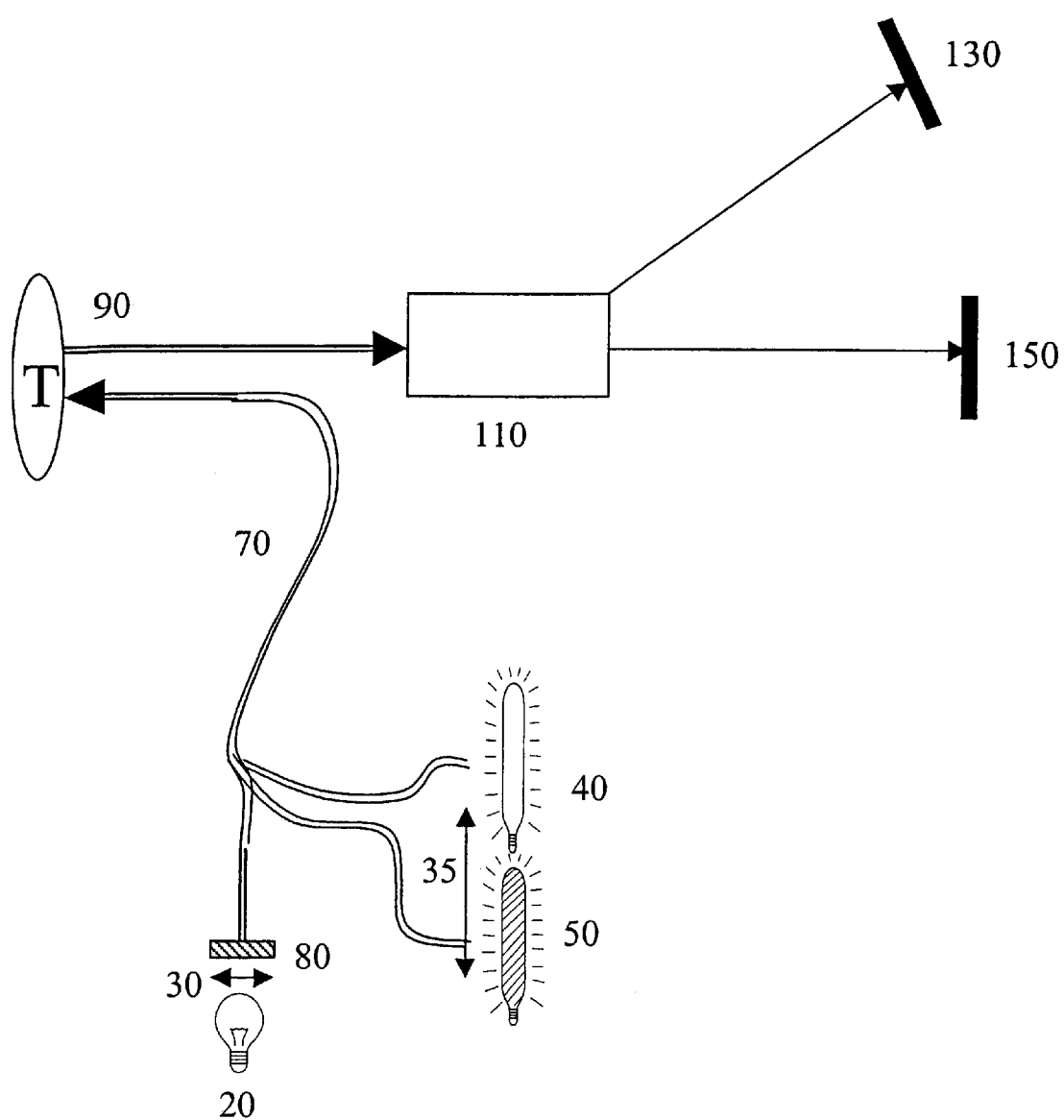
FIG. 5 is a schematic view of an alternative embodiment of a device according to the present invention in which markerless imaging light is combined with excitation light using fiber optics as an optical combiner.

FIG. 5 shows another alternative embodiment in which the marker excitation light 40 and autofluorescence excitation light 50 are combined with the markerless imaging light from the imaging light 20 and notch filter 80 using fiber optics as an optical combiner, instead of a dichroic mirror.

Figure 6:
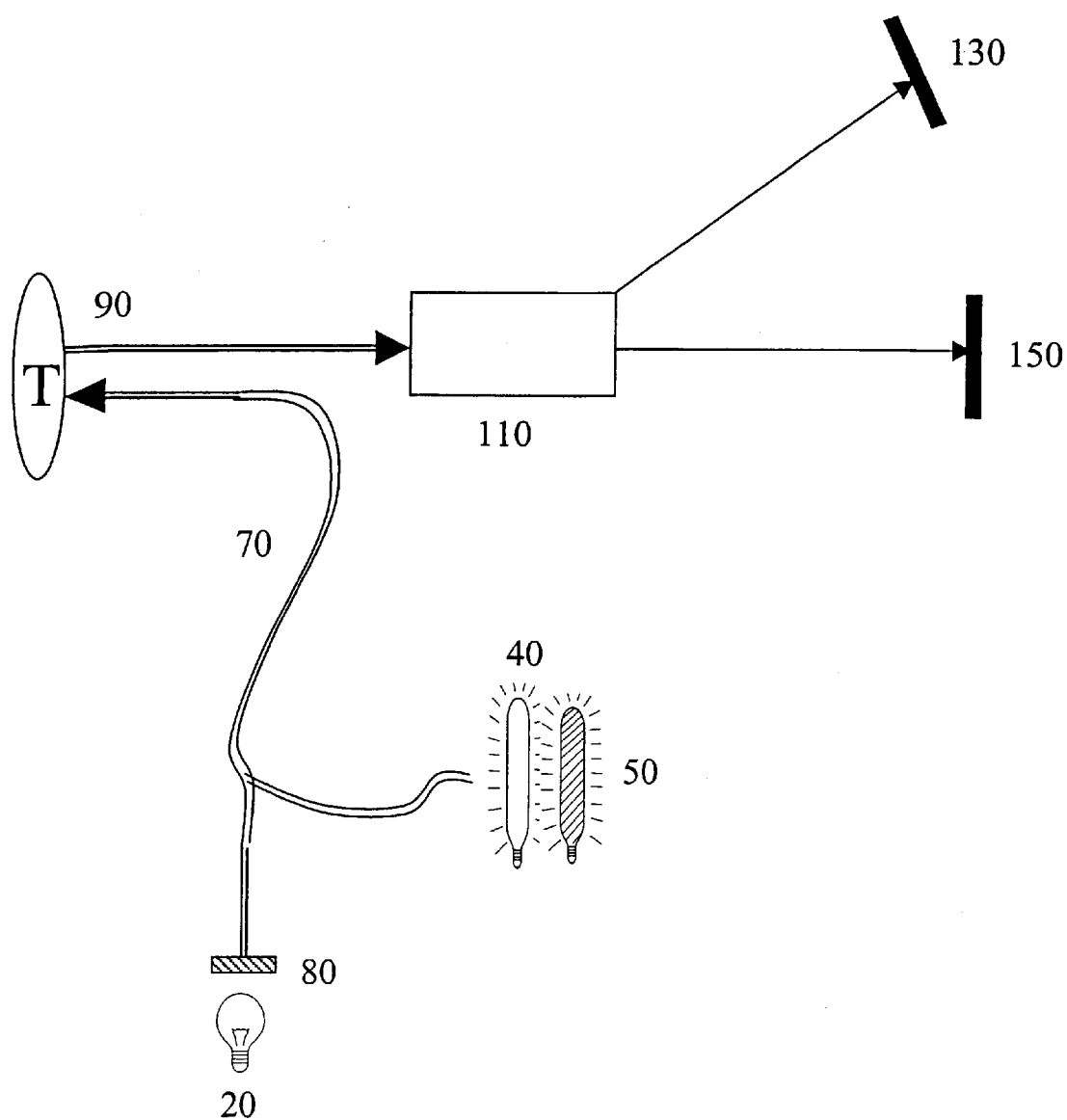
FIG. 6 is a schematic view of an alternative embodiment of a device according to the present invention in which the excitation lights and imaging light cycle on and off, instead of using shutters.

FIG. 6 shows another alternative embodiment in which the excitation lights and imaging light cycle on and off between the modes, instead of using shutters.

Figure 7:
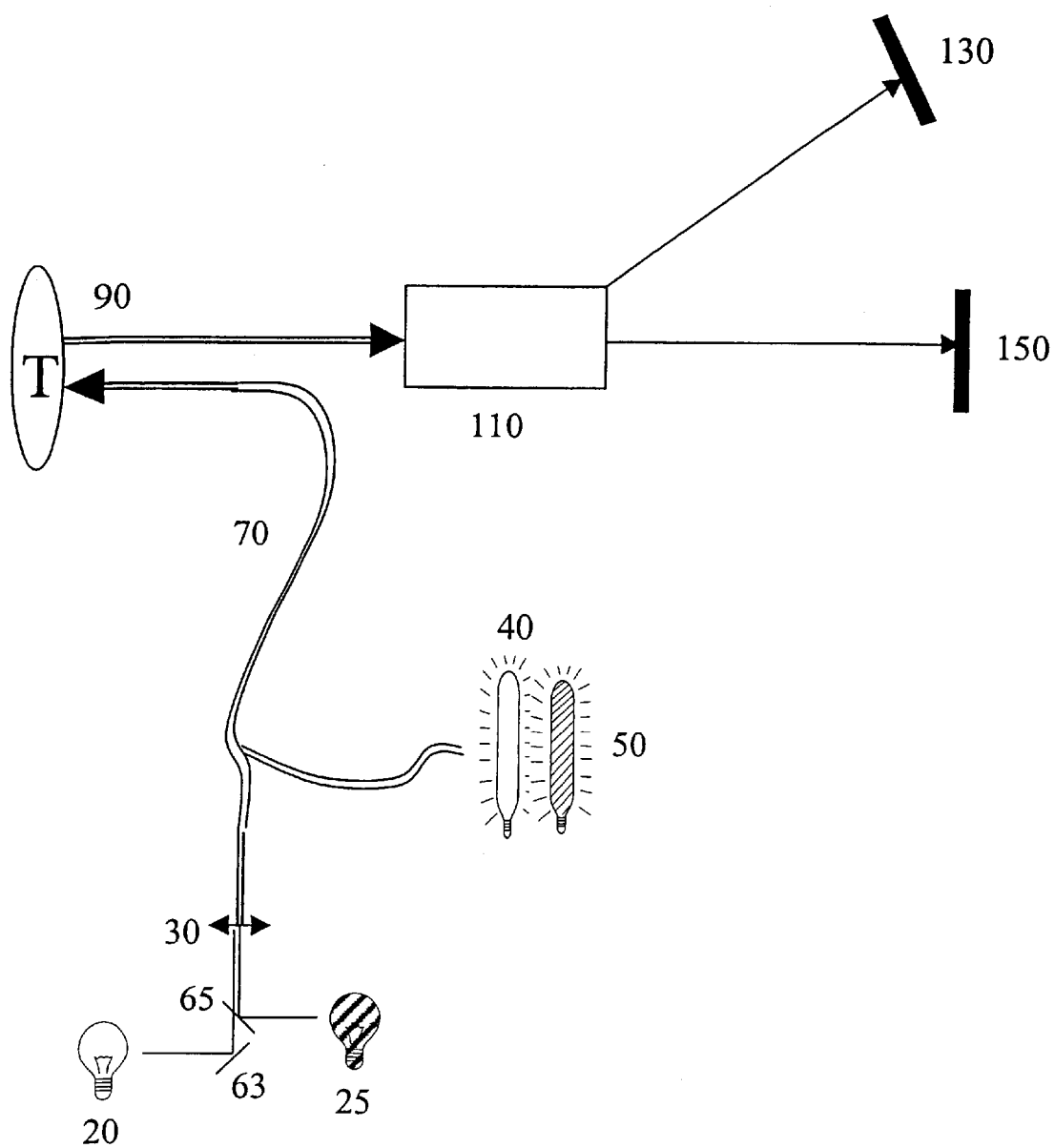
FIG. 7 is a schematic view of an alternative view of an alternative embodiment of a device according to the present invention in which lights having sharp spectral cutoffs on either side of the marker wavelength are combined to provide markerless imaging light free of the marker wavelength.

FIG. 7 shows still another alternative embodiment in which imaging lights 20 and 25 have sharp spectral cutoffs on either side of the marker wavelength: one has wavelengths longer than the marker wavelength and the other has wavelengths shorter than the marker wavelength. The lights from the imaging lights 20 and 25 are combined by an optical combiner (dichroic mirros 63 and 65 are shown, but fiber optics or other combiners can be used instead) to provide markerless imaging light. Excitation light from the marker excitation light 40 and autofluorescence excitation light 50 are transmitted using one fiber optic cable and the markerless imaging light is transmitted using another.

Of course, various alternative arrangements and combinations of shutters, mirrors, light sources and adjustable narrow band filters are within the skill of an ordinary artisan and the scope of the invention, and the specific arrangement is not critical, as long as the appropriate illumination and imaging conditions are achieved during the scanning and analysis modes.

Preferably the device of the invention would be used with a commercially available endoscope, although illuminating fibers would need to be substituted that efficiently transmit excitation light, such as blue, violet or ultraviolet light.

Preferably, standard imagers could be used, including CCDs with binned pixels.

Hyperspectral resolution of less than 10 nm would be preferred to avoid the convolving (interfering) effects of other environmental substances in the tissues.

Optionally, a dosage monitor could be added to monitor the dosage of ultraviolet light introduced by the device.

Optionally also, an analog, digital or other recorder (such as a videotape or DVD, for example) could be added to record the data collected by the device.

In use, a patient would preferably be provided with ALA. The device, preferably installed in an endoscope or fiber optic probe containing both a high resolution imaging fiber optic bundle and separate illuminating fiber optics, would then be used to screen the intestinal surface for polyps or other abnormal tissue, using illumination from both the imaging light 20 and marker excitation light 40. The marker excitation light 40 would cause the PpIX to fluoresce at approximately 640 nm. However, light at that spectral band would have been removed from the imaging light by the notch filter 80, so that light in that band would be from the PpIX that localized in suspicious areas. The adjustable narrow band filter 110 would then separate out light at the marker wavelength, approximately 640 nm, and direct that marker light to a highly sensitive monochromatic CCD 130, with the remaining light sent to the high-resolution color CCD 150. Preferably, the image of the tissue at the marker wavelength would then be overlaid on top of the image of the tissue in the markerless imaging light so that potentially abnormal tissues would be clearly identifiable in the combined image.

Alternatively, instead of administering an exogenous fluorescent marker and providing excitation light in a screening mode, screening can be performed using conventional visual inspection (without fluorescent markers or excitation light for the markers), or pre-segmentation analyses (that is, setting adjustable thresholds of characteristics to define segments of images) can be performed on visible light images to delineate the areas of highest probability of abnormality. In other words, image processing software can analyze visible light images based on characteristics differentiating normal from abnormal tissue in visible light and segment the visible light images into areas of highest probabilities of abnormality, so as to identify "suspicious" areas. This image processing is described in patent application Ser. No. 60/410192, filed on Sep. 13, 2002, entitled "A Method for Classifying Normal and Abnormal Tissues in Fluorescence and Reflectance Imagery Using both Spectral and Image Processing" by Michael James DeWeert, Ulf Gustafsson, Gary Bignami, Johan Hakansson, Ellen Jacobsen, Elisabeth McLaughlin, Rolf Wolters, Paul Troy, and Carl Johnson, which is incorporated herein by reference. These characteristics in visible light are well known, such as discolorations or inflammations or structural anomalies, and these characteristics are conventionally used by doctors performing normal visual examinations. Thus, the goal of pre-segmentation analysis is to reproduce and automate the visual screening of an experienced doctor.

Referring to FIG. 1, in an analysis mode, once an area of potentially abnormal tissue is identified in the screening mode, the imaging light source 20 would be shuttered by the shutter 30 and (preferably) the marker excitation light 40 cycled off (or, alternatively, blocked by the excitation shutter (s) 35), and the tissue T would be illuminated only by the autofluorescence excitation light 50. The adjustable narrow band filter 110 would then collect images of the tissue T at the selected differentiating portions of the autofluorescence spectrum of the tissue and separate images at each of the selected bands would be synchronously collected by the monochromatic CCD. Those separate images could then be compared by image processing software at each pixel for spectral characteristics that would differentiate abnormal tissue from normal tissue, such as relative intensity or spectral peak ratios or other characteristics known in the art (or a reference band could be used for normalization, as described above). The image processing software could then provide an image that delineates those areas of the tissue T in which the differentiating portions of the autofluorescence spectra indicate the presence of abnormal tissue. Of course, false color images could also be synthesized for ease of analysis and diagnosis, as described above.

To summarize the illumination cycle, during the screening mode, the tissues would be illuminated by both the imaging light and the marker excitation light, but during the analysis mode, the tissues would be illuminated only by the autofluorescence excitation light.

Alternatively, if screening is performed using processing of the imaging image (and not an exogenous fluorescent marker), then during the screening mode, only the imaging light would be used, and during the analysis mode, only an excitation light (preferably selected to maximize autofluorescence) would be used.

Because in the analysis mode, spectral information is only collected at the differentiating portions of the autofluorescence spectra, the device does not need to collect full spectral data from the tissue T. Only selected spectral data is collected and analyzed, as opposed to other devices and processes that collect full spectral data and then analyze only part of the collected spectral data. This correspondingly reduces the amount of time necessary to acquire the spectral full-area images, thus reducing the exposure time necessary to acquire the images needed to differentiate abnormal tissue from normal tissue. Thus, full-area data is provided over the entire field of view of the endoscope, and only selected spectral data is acquired, which allows a "virtual biopsy" of those areas indicated as potentially abnormal in screening mode. Limiting the amount of exposure may be desirable, especially if the patient has been photosensitized by an exogenous fluorescent marker or otherwise. Further, preferably approximately 5 spectral bands are collected and analyzed, and at least one of the spectral bands of the selected spectral data is 10 nm or less in width.

Conventional endoscopes, colonoscopes and other imaging instruments can easily be adapted for use of this invention by modifying their illumination light guides to provide high transmissivity of the excitation lights 40 and 50. It is preferred that the form, size, shape and other mechanical characteristics of devices according to this invention be identical to the mechanical characteristics of conventional imaging instruments so that users can use the devices in their customary manner, yet achieve the screening and analysis (virtual biopsy) advantages of this invention.

While the present invention has been disclosed in connection with the presently preferred best mode described herein, it should be understood that there may be other embodiments which fall within this spirit and scope of the invention as defined by the claims. For example, the excitation light need not be ultraviolet, but instead could be blue light, which also causes ALA to fluoresce. This may be preferable due to regulatory reasons that limit the ability to expose patients to ultraviolet light. For still another example, the present invention shall not be limited by size, materials, connection methods, optical attachments (i.e., endoscopes, colposcopes, cytoscopes, etc.) or specified target tissues, objects or materials. Accordingly, no limitations are to be implied or inferred n this invention except as specifically and as explicitly set forth in the claims.

Industrial Applicability

This invention can be used whenever it is desired to screen for areas that exhibit different fluorescence when treated with an exogenous fluorescent marker (or can be screened using image processing or conventional visual examination), and then to analyze autofluorescence to differentiate normal areas from abnormal areas, while minimizing time for acquiring spectral images. These include fields such as gastroenterology, bronchoscopy or other similar fields and includes applications to a wide range of pre-malignancies, dysplastic lesions and superficial tumors.

The techniques of this invention can also be applied in veterinary or other biological applications for medical, research and industrial use.

What is claimed is:

1. A dual mode device for real-time screening and rapid full-area, selective-spectral, remote imaging and analysis to differentiate normal tissues having a normal fluorescence spectrum from abnormal tissues having an abnormal fluorescence spectrum that differs from said normal fluorescence spectrum at differentiating portions when said tissues are excited by an excitation light, wherein said abnormal tissues emit fluorescent light at a marker wavelength when said tissues are treated with an exogenous fluorescent marker that selectively localizes in said abnormal tissue and when said tissues are excited by said excitation light, comprising:

an imaging light source emitting imaging light;
a closable shutter to selectively block said imaging light during an analysis mode;
a marker filter spaced apart from said imaging light that filters light of said marker wavelength from said imaging light to create markerless imaging light;
an excitation light source emitting excitation light;
an optical combiner combining said markerless imaging light and said excitation light;
an illumination light guide that guides said markerless imaging light and said excitation light to illuminate said tissues;
whereby, when said shutter is opened, said device is in a screening mode and said tissues are illuminated with both markerless imaging light and said excitation light and said tissues reflect said markerless imaging light to form reflected light and whereby said abnormal tissues fluoresce at said marker wavelength to form fluorescent light;

whereby, when said shutter is closed, said device is in said analysis mode and said tissues are illuminated only with said excitation light and said normal tissues fluoresce with said normal fluorescence spectrum and said abnormal tissues fluoresce with said abnormal fluorescence spectrum that differs from said normal fluorescence spectrum at said differentiating portions;
a high resolution imager to provide full area images of said tissues;
a sensitive imager to provide full area images of said tissues; and
an adjustable narrow band filter interposed between said tissues and said imagers that:
in said screening mode, separates and directs said fluorescent light with said marker wavelength to said sensitive imager to form a marker image, and that separates and directs said reflected light to said high resolution imager to form an imaging image;
in said analysis mode, deflects multiple selected narrow bands of said differentiating portions to said sensitive imager to form multiple full area selective-spectral images, whereby collecting full spectral information is avoided;
an image processor operably connected to said imagers that combines and processes data from said imagers approximately in real time that:
in said screening mode, allows comparison between said marker image and said imaging image by a method selected from the group consisting of a false color overlay of said marker image over said imaging image, displaying said marker image side by side with said imaging image, and alternately displaying said marker image and said imaging image; and
in said analysis mode, analyzes said multiple full area selective-spectral images and differentiates said normal tissue from said abnormal tissues.

2. A dual mode device for real-time screening and rapid full-area, selective-spectral, remote imaging and analysis to differentiate normal tissues having a normal fluorescence spectrum from abnormal tissues having an abnormal fluorescence spectrum that differs from said normal fluorescence spectrum at differentiating portions when said tissues are excited by an excitation light, comprising:

an activatable imaging light source emitting imaging light during a screening mode;
an activatable excitation light source emitting excitation light during an analysis mode;
an illumination light guide that guides said imaging light and said excitation light to illuminate said tissues;
whereby, when said imaging light is activated, said excitation light is deactivated, said device is in a screening mode and said tissues are illuminated with said imaging light that reflects from said tissues to form reflected light;
whereby, when said excitation light is activated, said imaging light is deactivated, said device is in said analysis mode and said tissues are illuminated only with said excitation light and said normal tissues fluoresce with a normal fluorescence spectrum and said abnormal tissues fluoresce with said abnormal fluorescence spectrum that differs from said normal fluorescence spectrum at said differentiating portions;
a high resolution imager to form full area images of said tissues;
a sensitive imager to form full area images of said tissues; and an adjustable narrow band filter interposed between said tissues and said imagers that:
in said screening mode, separates and directs said reflected light to one of said imagers to form a screening image;
in said analysis mode, deflects multiple selected narrow bands of said differentiating portions to said sensitive imager to form multiple full area selective-spectral images, whereby collecting full spectral information is avoided;
an image processor operably connected to said imagers that, in approximately real time:
in said screening mode, performs a pre-segmentation analysis to segment said screening image into suspicious areas; and
in said analysis mode, analyzes said multiple full area selective-spectral images and differentiates said normal tissue from said abnormal tissue.

3. A device for area imaging and spectroscopically distinguishing normal tissues having a normal fluorescence spectrum from abnormal tissues having an abnormal fluorescence spectrum that differs from said normal fluorescence spectrum at differentiating portions when said tissues are excited by an excitation light, wherein said abnormal tissues fluoresce differently from said normal tissues at a marker wavelength when said tissues are treated with an exogenous fluorescent marker that selectively localizes in said abnormal tissue and when said tissues are excited by said excitation light, comprising:
an activatable imaging light source activatably emitting imaging light when in a screening mode;
an excitation light source emitting excitation light in both said screening mode and an analysis mode, wherein said excitation light is selected from the group consisting of blue light, violet light and ultraviolet light;
an optical combiner that combines said imaging light and said excitation light;
a narrow band filter that removes light at said marker wavelength from said imaging light, resulting in markerless imaging light;
an illuminating light guide that directs said markerless imaging light and said excitation light onto said tissues, whereby in said screening mode said tissues are illuminated with said markerless imaging light and said excitation light, said tissues reflect said markerless imaging light to form reflected light, and said abnormal tissues fluoresce at said marker wavelength, and whereby in said analysis mode said tissues are illuminated only with said excitation light, and said abnormal tissues fluoresce differently from said normal tissues at said differentiating portions;
an imaging bundle positioned to transmit images of said tissues as so illuminated;
a monochromatic CCD;
a high resolution color CCD;
an adjustable narrow band filter operably connected to said imaging bundle that:
in said screening mode, directs light from said tissues at said marker wavelength to said monochromatic CCD to form a marker image and directs said reflected light from said tissues to said color CCD to form an reflected light image; and
in said analysis mode, directs said multiple narrow bands of said differentiating portions to said monochromatic CCD, whereby collecting full spectral information is avoided;
an image processor operably connected to said CCDs that combines data from said CCDs in approximately real time that:
in said screening mode displays and compares said marker image from said monochromatic CCD and said reflected light image from said color CCD using a method selected from the group consisting of a false color overlay of said marker image over said reflected light image, displaying said marker image next to said reflected light image, and alternately displaying said maker image and said reflected light image;
in an analysis mode, analyzes said multiple narrow bands of differentiating portions and differentiates said normal tissue from said abnormal tissue to form a differentiated image and displays and compares said differentiated image and said reflected light image using a method selected from the group consisting of a false color overlay of said differentiated image over said reflected light image, displaying said differentiated image next to said reflected light image, and alternately displaying said reflected light image and said differentiated image.

4. A device for area imaging and spectroscopically distinguishing normal tissues having a normal fluorescence spectrum from abnormal tissues having an abnormal fluorescence spectrum that differs from said normal fluorescence spectrum at differentiating portions when said tissues are excited by a an autofluorescence excitation light, wherein said abnormal tissues fluoresce differently from said normal tissues at a marker wavelength when said tissues are treated with an exogenous fluorescent marker that selectively localizes in said abnormal tissue and when said tissues are excited by a marker excitation light, comprising:
an activatable imaging light source activatably emitting imaging light when in a screening mode;
an activatable marker excitation light source activatably emitting marker excitation light when in said screening mode;
an activatable autofluorescence excitation light source emitting autofluorescence excitation light when in an analysis mode, wherein said autofluorescence excitation light is selected from the group consisting of blue light, violet light and ultraviolet light;
a dichroic mirror that combines said imaging light and said marker excitation light when in said screening mode;
a narrow band filter that removes light at said marker wavelength from said imaging light, resulting in markerless imaging light;
an illuminating light guide that directs said markerless imaging light and said marker excitation light onto said tissues when in said screening mode, and that directs said autofluorescence excitation light onto said tissues when in said analysis mode,
whereby in said screening mode said tissues are illuminated with said markerless imaging light and said marker excitation light, said tissues reflect said markerless imaging light to form reflected light, and said abnormal tissues fluoresce at said marker wavelength, and
whereby in said analysis mode said tissues are illuminated only with said autofluorescence excitation light, and said abnormal tissues fluoresce differently from said normal tissues at said differentiating portions;

an imaging bundle positioned to receive and transmit light from said tissues as so illuminated;

a monochromatic CCD;

a high resolution color CCD;

an adjustable narrow band filter operably connected to said imaging bundle that:

in said screening mode, directs light from said tissues at said marker wavelength to said monochromatic CCD to form a marker image and directs said reflected light from said tissues to said color CCD to form a reflected light image; and in said analysis mode, directs said multiple narrow bands of said differentiating portions to said monochromatic CCD, whereby collecting full spectral information is avoided;

an image processor operably connected to said CCDs that processes data from said CCDs in approximately real time that:

in said screening mode displays and compares said marker image from said monochromatic CCD and said reflected light image from said color CCD using a method selected from the group consisting of a false color overlay of said marker image over said reflected light image, displaying said marker image next to said reflected light image, and alternately displaying said marker image and said reflected light image;

in an analysis mode, analyzes said multiple narrow bands of differentiating portions and differentiates said normal tissue from said abnormal tissue to form a differentiated image and displays and compares said differentiated image and said reflected light image using a method selected from the group consisting of a false color overlay of said differentiated image over said reflected light image, displaying said differentiated image next to said reflected light image, and alternately displaying said differentiated image and said reflected light image.

5. A device for area imaging and spectroscopically distinguishing normal tissues having a normal fluorescence spectrum from abnormal tissues having an abnormal fluorescence spectrum that differs from said normal fluorescence spectrum at differentiating portions when said tissues are excited by a an autofluorescence excitation light, wherein said abnormal tissues fluoresce differently from said normal tissues at a marker wavelength when said tissues are treated with an exogenous fluorescent marker that selectively localizes in said abnormal tissue and when said tissues are excited by a marker excitation light, comprising:

an activatable visible light source activatably emitting visible light when in a screening mode;

an activatable marker excitation light source activatably emitting marker excitation light when in said screening mode;

an autofluorescence excitation light source emitting autofluorescence excitation light when in an analysis mode, wherein said autofluorescence excitation light is selected from the group consisting of blue light, violet light and ultraviolet light;

a dichroic mirror that combines said imaging light and said marker excitation light when in said screening mode;

a narrow band filter that removes light at said marker wavelength from said imaging light, resulting in markerless imaging light;

a fiber optic illumination bundle having ultraviolet transmissivity of at least 80% that directs said markerless imaging light and said marker excitation light onto said tissues when in said screening mode, and that directs said autofluorescence excitation light onto said tissues when in said analysis mode, whereby in said screening mode said tissues are illuminated with said markerless imaging light and said marker excitation light, said tissues reflect said markerless imaging light to form reflected light, and said abnormal tissues fluoresce at said marker wavelength, and whereby in said analysis mode said tissues are illuminated only with said autofluorescence excitation light, and said abnormal tissues fluoresce differently from said normal tissues at said differentiating portions;

a fiber optic imaging bundle positioned to receive and transmit light from said tissues as so illuminated;

a monochromatic CCD;

a high resolution color CCD;

an adjustable narrow band filter selected from the group consisting of an acousto-optical tunable filter, a liquid crystal tunable filter and a filter wheel operably connected to said imaging bundle that:

in said screening mode, directs light from said tissues at said marker wavelength to said monochromatic CCD to form a marker image and directs said reflected light from said tissues to said color CCD to form a reflected light image; and in said analysis mode, directs approximately 4 to approximately 9 narrow spectral bands selected from said differentiating portions to said monochromatic CCD, whereby collecting full spectral information is avoided;

an image processor operably connected to said CCDs that processes data from said CCDs in approximately real time that:

in said screening mode displays and compares said marker image from said monochromatic CCD and said reflected light image from said color CCD using a method selected from the group consisting of a false color overlay of said marker image over said reflected light image, displaying said marker image next to said reflected light image and alternately displaying said marker image and said reflected light image;

in an analysis mode, analyzes said 4 to 9 narrow spectral bands and differentiates said normal tissue from said abnormal tissue to form a differentiated image and displays and compares said differentiated image and said reflected light image using a method selected from the group consisting of a false color overlay of said differentiated image over said reflected light image, displaying said differentiated image next to said reflected light image, and alternately displaying said differentiated image and said reflected light image.

6. A dual mode device for real-time screening and rapid full-area, selective-spectral, remote imaging and analysis to differentiate normal tissues having a normal fluorescence spectrum from abnormal tissues having an abnormal fluorescence spectrum that differs from said normal fluorescence spectrum at differentiating portions when said tissues are excited by an excitation light, comprising:

an activatable imaging light source emitting imaging light;

a closable shutter to selectively block said imaging light during an analysis mode;

an activatable excitation light source emitting excitation light;

an illumination light guide that guides said imaging light and said excitation light to illuminate said tissues;

whereby, when said shutter is opened, said device is in a screening mode and said tissues are illuminated at least with said imaging light and said tissues reflect said imaging light to form reflected light;

whereby, when said shutter is closed, said device is in said analysis mode and said tissues are illuminated with said excitation light and said normal tissues fluoresce with a normal fluorescence spectrum and said abnormal tissues fluoresce with said abnormal fluorescence spectrum that differs from said normal fluorescence spectrum at said differentiating portions;

a high resolution imager to image said tissues;

a sensitive imager to image said tissues; and an adjustable narrow band filter interposed between said tissues and said imagers that:
  in said screening mode, directs said reflected light to said high resolution imager to form an imaging image;
  in said analysis mode, deflects multiple selected narrow bands of said differentiating portions to said sensitive imager to form multiple selective-spectral images, whereby collecting full spectral information is avoided;

an image processor operably connected to said imagers that combines data from said imagers approximately in real time that:
  in said analysis mode, analyzes said multiple selective-spectral images and differentiates said normal tissue from said abnormal tissue using a process selected from the group consisting of comparing ratios of spectral peaks at selected spectral bands, principal component analysis, minimum noise fraction, wavelet analysis, band ratio test and fractal pattern recognition;
  whereby screening for said abnormal tissue can be performed during said screening mode by a method selected from the group consisting of conventional visual inspection or pre-segmentation analysis of said imaging image.

7. A device according any one of claims 2 to 6, wherein at least one of said activatable light sources is selected from the group consisting of temperature stabilized LEDs with power cycled on during said screening mode and a light sources with activatable shutters opened during applicable modes.

8. A dual mode device for real-time screening and rapid full-area, selective-spectral, remote imaging and analysis to differentiate normal tissues having a normal fluorescence spectrum from abnormal tissues having an abnormal fluorescence spectrum that differs from said normal fluorescence spectrum at differentiating portions when said tissues are excited by an excitation light, comprising:

an excitation light source emitting excitation light during an analysis mode;

an illumination light guide that guides said excitation light to illuminate said tissues with said excitation light during said analysis mode;

whereby, when said tissues are illuminated with said excitation light, said normal tissues fluoresce with said normal fluorescence spectrum and said abnormal tissues fluoresce with said abnormal fluorescence spectrum that differs from said normal fluorescence spectrum at said differentiating portions;

a sensitive imager to provide full area images of said tissues; and an adjustable narrow band filter interposed between said tissues and said sensitive imager that, in said analysis mode, deflects multiple selected narrow bands of said differentiating portions to said imager to form multiple full area selective-spectral images, whereby collecting full spectral information is avoided; and an image processor operably connected to said imager that combines and processes data from said imager that, in said analysis mode, rapidly analyzes said multiple full area selective-spectral images to differentiate said normal tissue from said abnormal tissues, whereby a virtual biopsy of said tissues is performed.

9. A dual mode device for real-time screening and rapid full-area, selective-spectral, remote imaging and analysis to differentiate normal tissues having a normal fluorescence spectrum from abnormal tissues having an abnormal fluorescence spectrum that differs from said normal fluorescence spectrum at differentiating portions when said tissues are excited by an excitation light, wherein said abnormal tissues emit fluorescent light at a marker wavelength when said tissues are treated with an exogenous fluorescent marker that selectively localizes in said abnormal tissue and when said tissues are excited by said excitation light, comprising:

an imaging light source emitting markerless imaging light free of light of said marker wavelength during a screening mode;

an excitation light source emitting excitation light during said screening mode and during an analysis mode;

combining means for combining said markerless imaging light and said excitation light during said screening mode;

an illumination light guide that guides said markerless imaging light and said excitation light to illuminate said tissues;

whereby, when said device is in said screening mode, said tissues are illuminated with both said markerless imaging light and said excitation light and said tissues reflect said markerless imaging light to form reflected light and said abnormal tissues fluoresce at said marker wavelength to form fluorescent light;

whereby, when said device is in said analysis mode, said tissues are illuminated only with said excitation light, said normal tissues fluoresce with said normal fluorescence spectrum and said abnormal tissues fluoresce with said abnormal fluorescence spectrum that differs from said normal fluorescence spectrum at said differentiating portions;

a high resolution imager to provide full area images of said tissues;

a sensitive imager to provide full area images of said tissues; and an adjustable narrow band filter interposed between said tissues and said imagers that:
  in said screening mode, separates and directs said fluorescent light with said marker wavelength to said sensitive imager to form a marker image, and that separates and directs said reflected light to said high resolution imager to form an imaging image;
  in said analysis mode, deflects multiple selected narrow bands of said differentiating portions to said sensitive imager to form multiple full area selective-spectral images, whereby collecting full spectral information is avoided;

an image processor operably connected to said imagers that combines and processes data from said imagers that:

in said screening mode, approximately in real time, allows comparison between said marker image and said imaging image by a method selected from the group consisting of a false color overlay of said marker image over said imaging image, displaying said marker image side by side with said imaging image, and alternately displaying said marker image and said imaging image; and in said analysis mode, rapidly analyzes said multiple full area selective-spectral images to differentiate said normal tissue from said abnormal tissues.

10. A device according to any one of claims 1 to 6, 8 or 9, wherein at least one of said narrow bands of said differentiating portions is at most approximately 10 nm wide.

11. A device according to any one of claims 1, 2, 6, 8 or 9, wherein said image processor analyzes said multiple selective-spectral images and differentiates said normal tissue from said abnormal tissue using a process selected from the group consisting of comparing ratios of spectral peaks at selected spectral bands, principal component analysis, minimum noise fraction, wavelet analysis, band ratio test and fractal pattern recognition.

12. A device according to claim 11, wherein said illumination light guide has ultraviolet transmissivity of at least 80%.

13. A device according to claim 11, wherein said illumination light guide has ultraviolet transmissivity of approximately 95% of ultraviolet light between approximately 330 nm and approximately 400 nm.

14. A process for real-time screening and rapid full-area, selective-spectral, remote imaging and analysis to differentiate normal tissues having a normal fluorescence spectrum from abnormal tissues having an abnormal fluorescence spectrum that differs from said normal fluorescence spectrum at differentiating portions when said tissues are excited by an excitation light, wherein said abnormal tissues emit fluorescent light at a marker wavelength when said tissues are treated with an exogenous fluorescent marker that selectively localizes in said abnormal tissue and when said tissues are excited by said excitation light, comprising:

administering said exogenous fluorescent marker to said tissues;

(a) in a screening mode:

illuminating said tissues with said excitation light and with visible light free from light having said marker wavelength, whereby said tissues reflect said visible light to form reflected visible light and whereby said abnormal tissues emit marker fluorescent light at said marker wavelength;

separating said reflected visible light and said marker fluorescent light;

displaying an imaging image of said tissues from said reflected visible light;

displaying a marker image of said tissues from said marker fluorescent light;

(b) in an analysis mode:

illuminating said tissues with said excitation light, whereby said abnormal tissues fluoresce differently from said normal tissues at said differentiating portions;

selecting light in multiple spectral bands within said differentiating portions to form selective-spectral images, whereby collecting full spectral information is avoided;

processing said selective-spectral images to differentiate said normal tissue from said abnormal tissue using a method selected from the group consisting of comparing ratios of spectral peaks at selected spectral bands, principal component analysis, minimum noise fraction, wavelet analysis, band ratio test and fractal pattern recognition.

15. A process according to claim 14 wherein at least one of said bands of said differentiating portions is at most approximately 10 nm wide.

* * * * *